United States Patent
Tan et al.

(10) Patent No.: US 6,548,264 B1
(45) Date of Patent: Apr. 15, 2003

(54) COATED NANOPARTICLES

(75) Inventors: Weihong Tan, Gainesville, FL (US); Swadeshmukul Santra, Gainesville, FL (US); Peng Zhang, Gainesville, FL (US); Rovelyn Tapec, Gainesville, FL (US); Jon Dobson, Stroke-on-Trent (GB)

(73) Assignee: University of Florida

( * ) Notice: Subject to any disclaimer, the term of this patent is extended or adjusted under 35 U.S.C. 154(b) by 0 days.

(21) Appl. No.: 09/572,469

(22) Filed: May 17, 2000

(51) Int. Cl.$^7$ .............................................. G01N 33/553
(52) U.S. Cl. ..................... 435/7.21; 435/6; 435/7.5; 436/524; 436/525; 436/526; 436/527; 428/402; 428/402.2; 428/402.24; 428/403; 428/404; 428/405
(58) Field of Search ............................... 428/402, 402.2, 428/402.24, 403, 404, 405; 436/524, 525, 526, 527; 435/6, 7.5, 7.21

(56) References Cited

U.S. PATENT DOCUMENTS

| | | | |
|---|---|---|---|
| 4,054,465 A | 10/1977 | Ziobrowski | |
| 4,438,156 A | 3/1984 | Homola et al. | |
| 5,091,206 A | 2/1992 | Wang et al. | |
| 5,667,716 A | 9/1997 | Ziolo et al. | |
| 5,695,901 A | 12/1997 | Selim | |
| 5,874,111 A | 2/1999 | Maitra et al. | |
| 5,879,715 A | 3/1999 | Higgins et al. | |
| 5,958,329 A | 9/1999 | Brown | |
| 5,990,479 A | * 11/1999 | Weiss et al. | 436/546 |
| 6,103,379 A | 8/2000 | Margel et al. | |
| 6,306,610 B1 | * 10/2001 | Bawendi et al. | 435/7.1 |

OTHER PUBLICATIONS

*Scientific and Clinical Applications of Magnetic Carriers*, U. Häfeli, W. Schütt, J. Teller, and M.Zborowski (eds.) Plenum Press, New York, ch. 2, 4, 10, 16, 19, 22, 24, 34, 39, 40, 43(1997).

Philipse et al., "Magnetic Silica Dispersions: Preparation and Stability of Surface–Modified Silica Particles with a Magnetic Core," Langmuir, 1092–99, 1994.

Grüttner, C., et al., "New types of silica–fortified magnetic nanoparticles as tools for moleculare biology applications," Journal of Magnetism and Magnetic Materials, 194:8, 1999.

Correa–Durate, M., et al., "Control of Packing Order of Self–Assembled Monolayers of Magnetite Nanoparticles with and without SiO$_2$ Coating by Microwave Irradiation," Langmuir, 14:6430–6435, 1998.

(List continued on next page.)

Primary Examiner—Christopher L. Chin
(74) Attorney, Agent, or Firm—Akerman Senterfitt; Stanley A. Kim

(57) ABSTRACT

Disclosed are silica-coated nanoparticles and a process for producing silica-coated nanoparticles. Silica-coated nanoparticles are prepared by precipitating nano-sized cores from reagents dissolved in the aqueous compartment of a water-in-oil microemulsion. A reactive silicate is added to coat the cores with silica. Also disclosed are methods for functionalizing silica-coated nanoparticles for use in a variety of applications.

63 Claims, 4 Drawing Sheets

OTHER PUBLICATIONS

VanDerVoort, P., et al., "Silylation of the Silica Surface A Review," Journal of Liquid Chromatography and Related Technologies,19:2723–2752, 1996.

Cordek, J., et al., "Direct Immobilization of Glutamate Dehydrogenase on Optical Fiber Probes for Ultrasensitive Glutamate Detection," Anal Chem, 71, 1529–1533, 1999.

Chung, L., "A Fluorescamine Assay for Membrane Protein and Peptide Samples with Non–Amino–Containing Lipids," Anal Biochem. 1997,248,195.

Tiefenauer, L., et al., "Antibody–Magnetite Nanoparticles: In Vitro Characterization of a Potential Tumor–Specific Contrast Agent for Magnetic Resonance Imaging," Bioconjugate Chem. 4:347–352 (1993).

Sjøgren, C., et al., "Magnetic Characterization of Iron Oxides for Magnetic Resonance Imaging," MRM 31:268–272 (1994).

Third International Conference on the Scientific and Clinical Applications of Magnetic Carriers, Rostock, Germany (May 3–6, 2000).

Chang, S., et al., "Creation of Templated Complex Topological Morphologies in Colloidal Silica," J. Am. Chem. Soc., 116:6745–6747 (1994).

Chang, S., "Preparation and Properties of Tailored Morphology, Monodisperse Colloidal Silica—Cadmium Sulfide Nanocomposites," J. Am. Chem. Soc., 116:6739–6744 (1994).

Zhang, K., et al., "Synthesis and Characterization of Silica—Copper Oxide Composite Derived from Microemulsion Processing," Langmuir, 15:3056–3061 (1999).

* cited by examiner

COATED NANOPARTICLES

STATEMENT AS TO FEDERALLY SPONSORED RESEARCH

This invention was made with Government support under grant number N00014-98-1-0621 awarded by the Office of Naval Research and grant number NSF BIO-9871880 awarded by the National Science Foundation. The Government may have certain rights in the invention.

CROSS REFERENCE TO RELATED APPLICATIONS

Not applicable.

REFERENCE TO MICROFICHE APPENDIX

Not applicable.

FIELD OF THE INVENTION

The invention relates generally to the field of nanoparticles and methods of making nanoparticles. More particularly, the invention relates to silica-coated nanoparticles prepared by using microemulsions.

BACKGROUND OF THE INVENTION

Nanoparticles are very small particles typically ranging in size from as small as one nanometer to as large as several hundred nanometers in diameter. Their small size allows nanoparticles to be exploited to produce a variety of products such as dyes and pigments; aesthetic or functional coatings; tools for biological discovery, medical imaging, and therapeutics; magnetic recording media; quantum dots; and even uniform and nanosize semiconductors.

Nanoparticles can be simple aggregations of molecules or they can be structured into two or more layers of different substances. For example, simple nanoparticles consisting of magnetite or maghemite can be used in magnetic applications (e.g., MRI contrast agents, cell separation tools, or data storage). See, e.g., *Scientific and Clinical Applications of Magnetic Microspheres*, U. Häfeli, W. Schütt, J. Teller, and M. Zborowski (eds.) Plenum Press, New York, 1997; Sjøgren et al., Magn.Reson. Med. 31:268, 1994; and Tiefenauer et al., Bioconjugate Chem. 4:347, 1993. More complex nanoparticles can consist of a core made of one substance and a shell made of another.

Many different type of small particles (nanoparticles or micron-sized particles) are commercially available from several different manufacturers including: Bangs Laboratories (Fishers, Ind.); Promega (Madison, Wis.); Dynal Inc. (Lake Success, N.Y.); Advanced Magnetics Inc.(Surrey, U.K.); CPG Inc.(Lincoln Park, N.J.); Cortex Biochem (San Leandro, Calif.); European Institute of Science (Lund, Sweden); Ferrofluidics Corp. (Nashua, N.H.); FeRx Inc.; (San Diego, Calif.); Immunicon Corp.; (Huntingdon Valley, Pa.); Magnetically Delivered Therapeutics Inc. (San Diego, Calif.); Miltenyi Biotec GmbH (USA); Microcaps GmbH (Rostock, Germany); PolyMicrospheres Inc. (Indianapolis, Ind.); Scigen Ltd.(Kent, U.K.); Seradyn Inc.; (Indianapolis, Ind.); and Spherotech Inc. (Libertyville, Ill.). Most of these particles are made using conventional techniques, such as grinding and milling, emulsion polymerization, block copolymerization, and microemulsion.

Methods of making silica nanoparticles have also been reported. The processes involve crystallite core aggregation (Philipse et al., Langmuir, 10:92, 1994); fortification of superparamagnetic polymer nanoparticles with intercalated silica (Gruttner, C and J Teller, Journal of Magnetism and Magnetic Materials, 194:8, 1999); and microwave-mediated self-assembly (Correa-Duarte et al., Langmuir, 14:6430, 1998). Unfortunately, these techniques have not proven to be particularly efficient for consistently fabricating nanoparticles with a particular size, shape and size distribution.

SUMMARY OF THE INVENTION

The invention relates to a new method for preparing nanoparticles having a core enveloped by a silica ($SiO_2$) shell. Such silica-coated nanoparticles can be used, for example, as dye-doped particles, "pigmentless" pigment particles, metal particles, semiconductor particles, magnetic particles, and drug molecule particles.

The method employs a microemulsion, i.e., isotropic and thermodynamically stable single-phase system, to produce nanoparticles cores of a predetermined, very uniform size and shape. Cores produced using the microemulsion are then coated with silica using a silicating agent. The nanoparticles thus formed can be customized for a particular application by derivatizing various chemical groups onto the silica coating.

Accordingly, the invention features nanoparticles having a core and a silica shell enveloping the core. The nanoparticles can have a mean size of less than 1 micron (e.g., between 1 nm and 300 nm, or between 2 nm and 10 nm). In some variations, the nanoparticle cores can be magnetic and can include a metal selected from the group consisting of magnetite, maghemite, and greigite. In other variations, the core includes a pigment which can be an inorganic salt such as potassium permanganate, potassium dichromate, nickel sulfate, cobaltchloride, iron(III) chloride, or copper nitrate. Similarly, the core can include a dye such as Ru/Bpy, Eu/Bpy, or the like; or a metal such as Ag and Cd.

The invention also features nanoparticles with a silica shell that is derivatized with a functional group such as a protein (e.g., an antibody); a nucleic acid (e.g., an oligonucleotide); biotin; or streptavidin.

Also within the invention is a method of making coated nanoparticles. This method includes the steps of: providing a microemulsion; providing a first aqueous solution of a first reactant and a second aqueous solution of a second reactant (the first reactant and second reactant being selected such that a solid precipitate forms upon mixing the first and second reactants together in an aqueous environment); adding the first aqueous solution to a first aliquot of the microemulsion and the second aqueous solution to a second aliquot of the microemulsion; mixing together the first and second aliquots to form a reaction mixture that reacts to form nanoparticle cores; and adding a coating agent to the cores to form coated nanoparticles.

The microemulsion can be a water-in-oil microemulsion that can be made by mixing together water; a relatively polar liquid such as isooctane, n-hexane, or cyclohexane; a surfactant such as AOT, TX-100, and CTAB; and, in some cases, a cosurfactant such as n-hexanol. The coating agent can be a reactive silicate such as TEOS and APTS. In some variations, the method includes a step of derivatizing the silica shell with a functional group such as a protein (e.g., an antibody); a nucleic acid (e.g., an oligonucleotide); biotin; or streptavidin. Thus, the method of the invention can be used to make protein-derivatized, silica-coated nanoparticles having cores including a metal such as magnetite, maghemite, or greigite.

In another aspect, the invention features a method of identifying cells expressing a preselected molecule. This method includes the steps of: providing a plurality of silica-coated nanoparticles coated with a functional group that binds to a preselected molecule; providing a plurality of cells at least some of which express the preselected molecule; mixing the plurality of silica-coated nanoparticles with the plurality of cells to form a mixture; placing the mixture under conditions that allow the nanoparticles to bind to cells expressing the preselected molecule; and analyzing the cells for bound nanoparticles. In one variation of this method, the functional group is an antibody that specifically binds to the preselected molecule. In another variation, the silica-coated nanoparticles are fluorescent.

As used herein, the word "nanoparticle" means a particle having a diameter of between about 1 and 1000 nm. Similarly, by the term "nanoparticles" is meant a plurality of particles having an average diameter of between about 1 and 1000 nm.

For the purposes herein, a microemulsion is defined as a thermodynamically stable, optically isotropic dispersion of two immiscible liquids consisting of nanosize domains of one or both liquids in the other, stabilized by an interfacial film of surface-active molecules.

By reference to the "size" of a nanoparticle is meant the length of the largest straight dimension of the nanoparticle. For example, the size of a perfectly spherical nanoparticle is its diameter.

By the phrase "specifically binds" means that one molecule recognizes and adheres to a particular second molecule in a sample, but does not substantially recognize or adhere to other molecules in the sample. Generally, an antibody that "specifically binds" a preselected antigen is one that binds the antigen with a binding affinity greater than about $10^5$ to $10^6$ liters/mole.

As used herein, the phrase "functional group" means a chemical group that imparts a particular function to an article (e.g., nanoparticle) bearing the chemical group. For example, functional groups can include substances such as antibodies, oligonucleotides, biotin, or streptavidin that are known to bind particular molecules; or small chemical groups such as amines, carboxylates, and the like.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

DETAILED DESCRIPTION

The invention is based on a method for preparing silica-coated nanoparticles using a water-in-oil microemulsion. The method yields uniformly-sized particles composed of a core enveloped by a silica shell. The microemulsion is made by combining a relatively polar liquid such as water, a relatively non-polar liquid such as a liquid alkane, and one or more surfactants to form an isotropic, thermodynamically stable single-phase system. This system is comprised of a plurality of very small spherical water pools (i.e., reverse micelles) that serve as reactors for producing nanoparticle cores. After the cores are produced, they are coated with silica using a silicating agent such as tetraethylorthosilicate (TEOS). In some applications, the silica coating is derivatized with one or more functional groups to yield nanoparticles particularly suited for specific applications. The below described preferred embodiments illustrate various adaptations of the invention. Nonetheless, from the description of these embodiments, other aspects of the invention can be readily fashioned by making slight adjustments or modifications to the components discussed below.

Nanoparticle Characteristics

Figure 1:
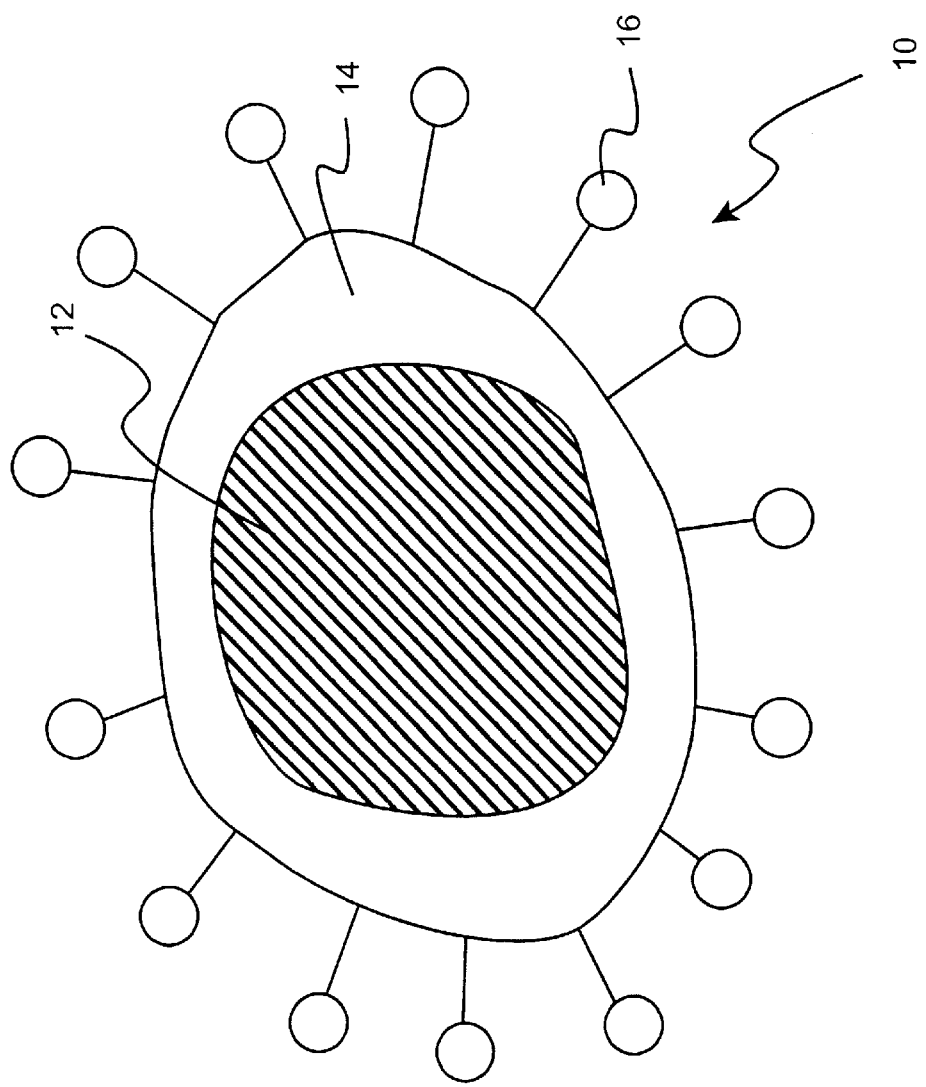
FIG. 1 is a cross-sectional view of a nanoparticle of the invention.

In brief overview, referring to FIG. 1, a preferred nanoparticle 10 of the invention includes a core 12, a shell 14 coating core 12, and one or more functional groups 16 derivatized onto shell 14. Although the diameter of nanoparticle 10 can range from about 1 nm to about 1000 nm or larger, for many applications it is preferably between about 10 nm to about 300 nm (e.g., about 10, 15, 20, 25, 30, 35, 50, 75, 100, 150, 200, 250, or 300 nm). In a dispersion of a plurality of nanoparticles 10, the size distribution preferably has a standard deviation of no more than about 25% (e.g., 1, 2, 3, 5, 10, 15, 20, and 25%) of the average diameter (or largest straight dimension) of the plurality of nanoparticles 10.

The nanoparticle 10 illustrated in FIG. 1 is solid (i.e., substantially without pores). While this form is preferred for many applications, nanoparticles within the invention can also be porous. Solid forms can be prepared as described below by uniformly coating core 12 with shell 14. Porous forms can be made by degrading a solid nanoparticle with a corrosive agent (e.g., a very basic solution where shell 14 is composed of silica), and optionally re-coating core 12 with silica. In general, solid forms are preferred when it is desired to sequester core 12 from the outside environment; whereas porous forms are preferred when it is desired to increase the surface area of shell 14 in contact with the outside environment (e.g., where nanoparticle 10 is used a catalyst) or sometimes when nanoparticle 10 is used to isolate various substances (e.g., for "trapping" substances within the pores). Pores in nanoparticle 10 can be of any suitable size less than the diameter of nanoparticle 10. For example, such pores can average about 0.2, 0.5, 1, 2, 3, 5, 10, 20, 50, or 100 nm in size.

Core 12 can be composed of any substance compatible with shell 14. As core 12 imparts functional characteristics on nanoparticle 10, one skilled in the art can select the composition of core 12 to suit the particular application intended for nanoparticle 10 based on known characteristics of compositions. For example, in a preferred embodiment where nanoparticle 10 is desired to be magnetic, core 12 is made up of a magnetic metal such as magnetite ($Fe_3O_4$), maghemite ($\gamma Fe_2O_3$), or greigite ($Fe_3S_4$). In this example, the composition of core 12 imparts a magnetic quality on nanoparticle 10 such that nanoparticle 10 can be used for magnetically based applications, e.g., cell separation/purification, diagnostic imaging, recording media, etc.

Depending on the particular application, magnetic core 12 can be either superparamagnetic or single-domain (i.e., with a fixed magnetic moment). Superparamagnetic particles are preferred in applications where particles having a fixed magnetic moment are not desired; whereas single-domain particles are preferred when particles having a fixed magnetic moment are desired, e.g., in magnetic recording media or for biomedical applications that require mechanical transduction (single-domain particles used to impart a torque).

For other applications, core 12 can be made up of non-magnetic metals or metal salts (e.g., gold, silver, cadmium sulfide, etc.). For example, nanoparticles having CdS cores coated with silica can function can be used as quantum dots, i.e., particles having charge carriers surrounded in all directions by potential barriers and which have quantized energy levels that can be used as highly flourescent or luminescent probes, or semiconductors. As another example, for the production of dye or pigment nanoparticles, core 12 can include inorganic salts useful in preparing "pigmentless" pigments, e.g., europium salts, tris(2,2'-bipyridyl) dichlororuthenium, potassium permanganate, potassium dichromate, nickel sulfate, cobalt chloride, iron(III) chloride, copper nitrate, etc.

Core 12 can also be composed of a mixture of different substances. For example, where it is desired to make a magnetic, dye-doped nanoparticle, core 12 can be composed of both a magnetic metal and an inorganic salt useful as a pigment. Where core 12 is composed of a material that is very soluble in common solvents (e.g., those typically used in paints and colored-coatings), it is especially desirable that such cores be coated with a substance that resists dissolution or degradation in such solvents.

Core 12 can be of any size less than the size of nanoparticle 10. Thus, core 12 can have a diameter of between less than 1 and 1000 nm. For many applications, core 12 preferably has a diameter ranging from about 1 to about 200 nm. As one example, because animals are able to excrete nanoparticles sized less than about 100 nm, but retain particles greater than 100 nm (primarily in the liver and spleen), cores small enough to be incorporated in nanoparticles less than 100 nm in size are preferred in diagnostic or therapeutic applications where is it desired that the nanoparticles not be retained in a subject.

When made using a microemulsion nanoparticle-manufacturing technique (see below), core 12 generally has a spheroid shape (conventional reverse micelles are spheroid). Core 12, however, is not limited to a spheroid shape. For example, rather than being perfectly round, nanoparticle 10 can be oblong or tube-like, a shape preferred in many magnetic applications. Where core 12 is in crystalline form, nanoparticle 10 can have a regular or irregular polyhedral shape such as a cuboid shape.

Shell 14 is a substance that coats core 12. It can be composed of any compatible material that can be coated onto core 12 using the methods of the invention. Shell 14 can, for example, be composed of a polymer (e.g., polystyrene, polyethylene, polyvinyl chloride, an acrylic polymer, etc.), a polysaccharide such as dextran, an inorganic oxide such as alumina or silica, or mixtures of the foregoing. In the presently preferred embodiment, shell 14 is composed partially or entirely of silica. Silica is preferred in various applications as it is relatively inert in many environments, is biocompatible, prevents agglomeration with other nanoparticles in a dispersion, and can be readily derivatized with many different function groups. And while FIG. 1 shows shell 14 configured in a single layer, it can also be multi-layered. For example, shell 14 can include a first layer of silica coating and immediately adjacent to core 12, and a second layer coating the silica layer. The second layer can be composed of any substance that be coated onto the first layer. For example, the second layer can be composed of a biodegradable material (e.g., a sugar or polymer) impregnated with a drug. When introduced to an animal, the biodegradable material and drug will gradually be dissolved into the animal. In other applications, shell 14 can be composed of 3, 4, 5 or more separate layers.

In the preferred embodiment shown in FIG. 1, shell 14 is shown completely enveloping core 12 and thus sequestering core 12 from the outside environment. This form is preferred where it desired to prevent interaction of core 12 with external factors. For example, a silica coating can prevent corrosion of an iron-based core. Similarly, a complete silica coating can enhance the shelf life a nanoparticle-based pigment by preventing degradation or dissolution of the pigment in a solvent or by oxidation. In some variations, nanoparticle 10 does not include a shell 14 or is only partially coated with a shell 14 (e.g., where shell 14 has been partially dissolved or degraded off core 12).

Shell 14 can be of any thickness (i.e., length from outside surface of core 12 to outside surface of shell 14) compatible with the methods of making nanoparticle 10. Using preferred methods of the invention, shell 14 can be made to have a thickness ranging from less than about 1 nm to greater than about 300 nm. Depending on the particular application that nanoparticle 10 is to be used in, the preferred thicknesses of shell 14 will vary. For example, a relatively thick shell is generally preferred where it is desired to reduce agglomeration of nanoparticles (where the cores attract one another) or degradation of the shell (e.g., in a caustic solvent). On the other hand, where it is desired to amplify the properties of the core (e.g., color of a pigment), a relatively thinner shell is generally preferred.

As shown in FIG. 1, functional groups 16 can be derivatized onto the surface of shell 14. Functional groups 16 can take the form of any chemical or biological group that can be attached to nanoparticle 10 via shell 14. For example, functional groups 16 can be one or more of proteins such as antibodies (monoclonal, polyclonal), enzymes, biotin, and streptavidin; nucleic acid molecules (e.g., RNA, DNA); chemosensors such as fluorescent probes; and biochemical groups such as amines and carboxylates.

Methods of Making Nanoparticles

Figure 2:
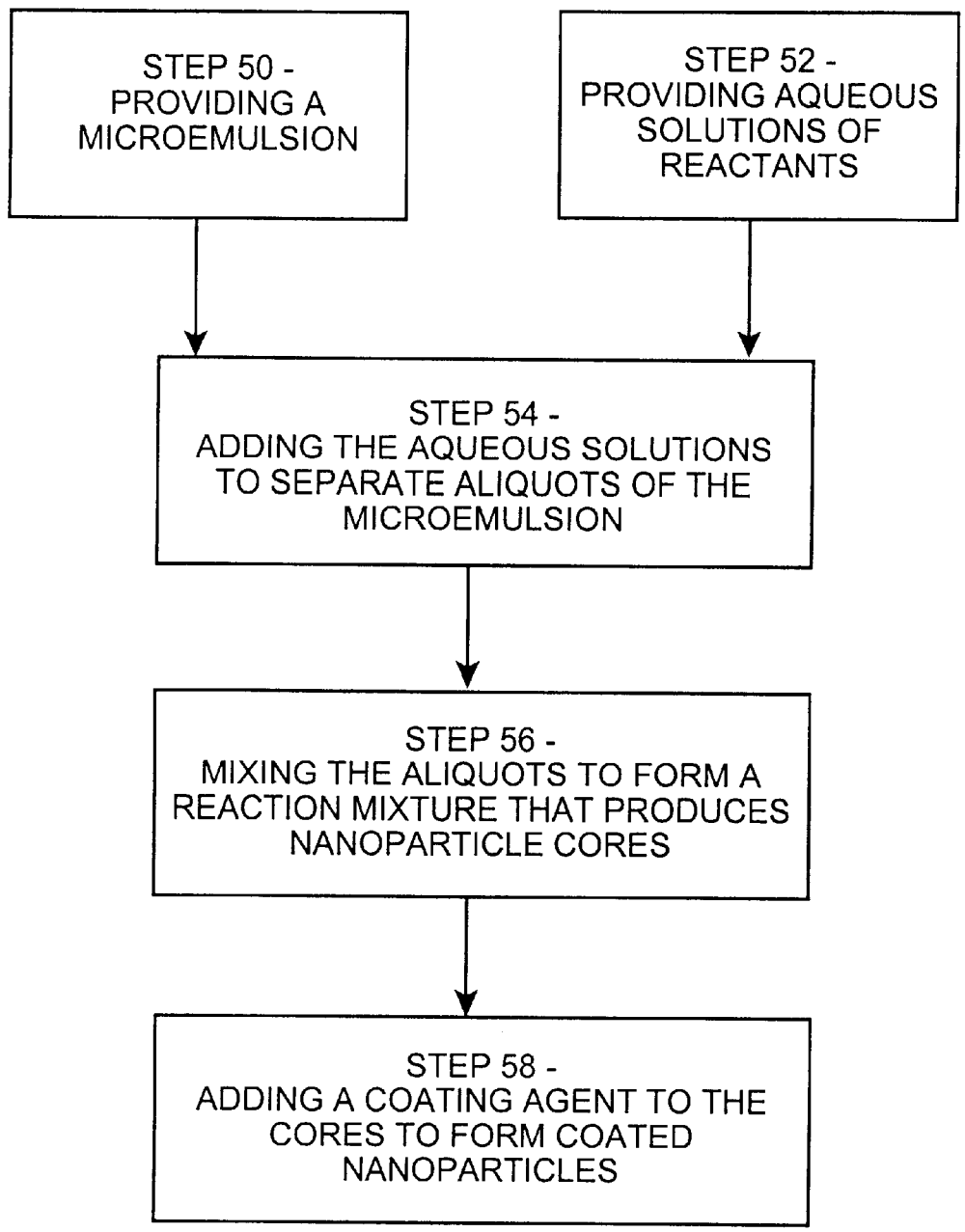
FIG. 2 is a flowchart illustrating general steps involved in a method of making nanoparticles of the invention.

Referring now to FIG. 2, a preferred method of making nanoparticles includes: a step 50 of providing a microemulsion; a step 52 of providing aqueous solutions of reactants; a step 54 of adding the aqueous solutions to separate aliquots of the microemulsion; a step 56 of mixing the aliquots to form a reaction mixture that produces nanoparticle cores; and a step 58 of adding a coating agent to the cores to form coated nanoparticles.

The microemulsion of step 50 can be made by mixing together at least two immiscible liquids in the presence of at least one surfactant to form a thermodynamically stable, optically isotropic dispersion of nanosize droplets of one or both liquids in the other. The dispersion is stabilized by the surfactant reducing the surface tension at the interface of the two liquids. Microemulsions can be either water-in-oil (i.e., reverse micelles or water droplets dispersed in oil), oil-in-water (i.e., micelles or oil droplets dispersed in water), or a bi-continuous system containing comparable amounts of two immiscible fluids. In some cases, microemulsions can be made by mixing together two non-aqueous liquids of differing polarity with negligible mutual solubility. For use in the invention water-in-oil microemulsion are presently preferred because they are compatible with very many known chemical reactions for precipitating solids in aqueous solutions.

The immiscible liquids that can be used in step 50 typically include a relatively polar (i.e., hydrophobic) liquid and a relative non-polar (i.e., hydrophillic) liquid. While a large variety of polar/nonpolar liquid mixtures can be used to form a microemulsion useful in the invention, the choice of particular liquids utilized will depend on the type of nanoparticles being made. A skilled artisan can select specific liquids for particular applications by adapting known methods of making microemulsions for use in the present invention. The presently preferred relatively polar liquid is water, although other polar liquids might also be useful. Water is preferred because it is inexpensive, readily available, non-toxic, easy to handle and store, compatible with a large number of different precipitation reactions, and immiscible in a large number of nonpolar solvents. Examples of suitale non-polar liquids include alkanes (e.g., any liquid form of hexane, heptane, octane, nonane, decane, undecane, dodecane, etc.), cycloalkanes (e.g., cyclopentane, cyclohexane, etc.), aromatic hydrocarbons (e.g., benzene, toluene, etc.), and mixtures of the foregoing (e.g., petroleum and petroleum derivatives). In general, any such non-polar liquid can be used as long as it is compatible with the other components used to form the microemulsion and does not interfere with the involved precipitation reaction.

Step 50 requires at least one surfactant to form a microemulsion. Surfactants are surface active agents that thermodynamically stabilize the very small dispersed micelles or reverse micelles in microemulsions. Typically, surfactants possess an amphipathic structure that allows them to form films with very low interfacial tension between the oily and aqueous phases. Thus, any substance that reduces surface tension at the interface of the relatively polar and relatively non-polar liquids and is compatible with other aspects of the invention can be used to form the microemulsion used to make nanoparticles. The choice of a surfactant will depend on the particular liquids utilized and on the type of nanoparticles being made. Specific surfactants suitable for particular applications can be selected from known methods of making microemulsions or known characteristics of surfactants. For example, non-ionic surfactants are generally preferred when an ionic reactant is used in the microemulsion process and an ionic detergent would bind to or otherwise interfere with the ionic reactant.

Numerous suitable surfactants are known. A nonexhaustive list includes soaps such as potasium oleate, sodium oleate, etc.; anionic detergents such as Aerosol® OT, sodium cholate, sodium caprylate, etc.; cationic detergents such as cetylpyridynium chloride, alkyltrimethylammonium bromides, benzalkonium chloride, cetyldimethylethylammonium bromide, etc; zwitterionic detergents such as N-alkyl-N,N-dimethylammonio-1-propanesulfonates and CHAPS; and non-ionic detergents such as polyoxyethylene esters, polyoxyethylene ethers, polyoxyethylenesorbitan esters, sorbitan esters, and various tritons (e.g., (TX-100, TX-114); etc.

The concentration of surfactant used in step 50 will depend on many factors including the particular surfactant selected, liquids used, and the type of nanoparticles to be made. Suitable concentrations can be determined empirically, i.e., by trying different concentrations of surfactant until the concentration that performs best in a particular application is found. Ranges of suitable concentrations can also be determined from known critical micelle concentrations.

In preferred embodiments bis (2-ethylhexyl) sulfosuccinate sodium salt (Aerosol® OT, AOT) is used to create a microemulsion of water and isooctane; cetyltrimethylammnonium bromide (CTAB) is used to create a microemulsion of n-hexane, n-hexanol, and water; and triton X-100 (TX-100) is used to make a microemulsion of cyclohexane, n-hexanol, and water.

Although, in most applications the invention, step 50 employs only one surfactant to stabilize the microemulsion, one or more cosurfactants can also be used. The use of a cosurfactant is sometimes advantageous for stabilizing reverse micelle systems. For example, adding an aqueous surfactant such as soap to a mixture of oil and water yields a milky emulsification. Adding a co-surfactant such as an alcohol of intermediate chain length causes the milky emulsion to clear spontaneously due to formation of very small spheres of dispersed water droplets in oil. Such cosurfactants function by further reducing the interfacial tension between the phases to facilitate the formation of very small particles of dispersed phase. Suitable co-surfactants for use in the invention include hexanol, butanol, pentanol, octanol, and like intermediate chain length alcohols.

The microemulsion of step 50 is prepared by simply mixing together a relatively polar liquid, a relatively non-polar liquid, and one or more surfactants. For preparing a water-in-oil microemulsion (having aqueous reverse micelles), the volume of the relatively non-polar liquid vastly exceeds that of the relatively polar liquid (e.g., non-polar liquid:polar liquid volume ratio between about 10000:1 to 100:1). While addition of the surfactant can sometimes cause a microemulsion to form without further agitation, generally the mixture is mechanically (e.g., magnetically) stirred or ultrasonicated to form the microemulsion. Many microemulsions useful in the invention can be prepared at room temperature (i.e., about 20° C.) without addition of heat. In other cases, to hasten microemulsion formation by increasing the solubility of the surfactant in the liquids, the mixture of ingredients is sometimes heated (e.g., using a hot plate) to between about 25–80° C.

Referring again to FIG.2, step 52 of providing aqueous solutions of reactants and step 54 of adding the aqueous solutions of step 52 to separate aliquots of a microemulsion can be performed using a water-in-oil microemulsion prepared as described above. Steps 52 and 54 can be accomplished by first providing a first water-soluble reactant (reactant A) and a second water-soluble reactant (reactant B), and then adding reactant A to a first aliquot of a water-in-oil microemulsion and reactant B to a second aliquot of a water-in-oil microemulsion. The two aliquots are separately mixed until reactant A reaches equilibrium distribution in each reverse micelle (reverse micelles continuously form, coalesce, and break apart in the microemulsion, thereby allowing any reactant contained therein to be distributed equally among the reverse micelles) of the first aliquot, and reactant B reaches equilibrium distribution in each reverse micelle of the first aliquot. In step 56, after allowing for the distribution of the dissolved species to equilibrate, the two aliquots are mixed together. Due to collision and coalescence of the reverse micelles, the cations of reactant A and anions of reactant B contact each other and react to form precipitates that serve as nanoparticle cores.

Reactants A and B are generally selected so that they can react to form a precipitate within the reverse micelles of the microemulsions. They are typically soluble in the aqueous reverse micelles and may be solids, liquids, or gases. In a preferred embodiment, Reactant A is a salt (e.g., with the hypothetical formula A$^+$X$^-$) that dissolves into soluble cations (e.g., A$^+$'s) within the reverse micelles of the first aliquot of the microemulsion, and Reactant B is another salt (e.g., with the hypothetical formula B$^+$Y$^-$) that dissolves into soluble anions (e.g., Y$^-$'s) within the reverse micelles of the second aliquot of the microemulsion. The cations of Reactant A and anions of Reactant B are selected so that they form a precipitate (A$^+$Y$^-$)when mixed together in an aqueous solution.

While the foregoing illustrates a preferred method of the invention, other methods for making nanoparticle cores using microemulsions are also within the invention. Many of these can be performed by making slight modifications to the preferred method just described. For example, rather than mixing together two different aliquots of a microemulsion, the core-forming reaction can be carried out using a single aliquot of a microemulsion. In this case, a reactant can be added to the single aliquot and allowed to dissolve and equilibrate among the reverse micelles of the microemulsion. Subsequently, a precipitating (e.g., reducing-or oxidizing) agent in the form of a liquid or gas (e.g., hydrogen, hydrazine, NH$_4$OH) is added to the single aliquot to precipitate the reactant dissolved in the reverse micelles.

Nanoparticle cores can be isolated from a microemulsion by adding a solvent such as acetone or ethanol to the microemulsion and then filtering and/or centrifuging the mixture to isolate the nanoparticles. For filtering, filters have pores sized smaller than the nanoparticles. For centri-fuging, the mixture can be spun at 10,000 RPM or more in a microcentrifuge for 15 minutes or more to pellet the nanoparticles and the supernatant can be decanted. Nanoparticles isolated in this manner can be washed one or more times with acetone or an ethanol/water solution to remove any surfactant or other microemulsion component. The isolated and washed nanoparticles can be dried over acetone. Prior to use or functionalization, the nanoparticles can be resuspended in an appropriate liquid.

Using the water-in-oil microemulsion technique, nanoparticle core size is highly controllable. Although core size generally relates to reverse micelle size, this is not necessarily a strict relationship as core size does not always correlate with the amount of reactant(s) originally present in each reverse micelle. For example, even small nanoparticle cores (e.g., having diameters of 2 nm to 5 nm) contain from about 300 to 1000 atoms, which is in most cases appreciably larger than the number of reactant molecules present in each micelle prior to reaction. This indicates that nanoparticle core nuclei first form in a small fraction of micelles; these then consume the reactant(s) in other micelles through collision-coalescence processes.

A factor to consider in nanoparticle core preparation therefore is the rate at which nanoparticle cores form. The rate at which nanoparticle cores form directly relates to the rate at which the reverse micelles coalesce. Thus, the specific surfactant selected strongly influences the core formation rate, controlling the rate of reverse micelle coalescence. That is, surfactants that result in a relatively rigid interface between the two immiscible liquids of the microemulsion decrease the core formation rate, while surfactants that result in a fluid interface increase the rate. Other properties of the microemulsion, such as ionic strength, pH, and temperature can also be manipulated to control the rate of core formation.

Through empirical adjustment of initial reactant concentrations and microemulsion compositional parameters, nanoparticle cores with homogeneous size distribution (e.g., percentage standard deviation in core size is between about 1 and 5% (for instance, 1, 2, 3, 4, and 5%)) and average diameters ranging from about 1 nm to about 300 nm or more. Cores of larger size (e.g., about 1 micron) can be prepared by: (i) adding a higher concentration of reagent(s) to the reaction medium (e.g., reverse micelles of the microemulsion), and/or (ii) sonochemically (i.e., by ultrasonication) dispersing isolated cores in a suitable solvent other than microemulsion to make a uniform core suspension, and then adding additional reagent to the dispersion. In the latter method, individual cores often fuse.

In most cases, nanoparticle cores made according to the water-in-oil microemulsion technique described above have a spheroid shape (conventional reverse micelles are spheroid). By altering various parameters in the core formation process, it is possible to produce cores having other shapes. For example, oblong or tube-shaped cores can be made by adding very high concentration of sodium dodecyl sulfate to the microemulsion. As another example, where reactants are selected such that the formed cores have a crystalline structure, nanoparticle cores having a regular or irregular polyhedral shape can be made.

Magnetic nanoparticles can be made using magnetic materials such as magnetite, maghemite, and greigite as part of the core. By varying the overall size and shape of such magnetic cores, they can be made superparamagnetic or stable single-domain (particles that retain a stable magnetic moment after being removed from a magnetic field). Core size relates to whether a magnetic nanoparticle is superparamagnetic or single-domain. Thus, relatively equidimensional superparamagnetic particles generally have a core sized less than 50 to 80 nm. At particle sizes above this upper range, the magnetization of the particle is split into domains of differing magnetization vectors in order to minimize internal magnetic energies.

Referring once again to FIG. 2, methods of making nanoparticles within the invention feature a step 58 of adding a coating agent to form coated nanoparticles. The coating agent used in step 58 can be any that causes silica (or another substance) to be deposited onto the surface of the nanoparticle cores. Presently preferred reagents include reactive silicates such as tetraethylorthosilicate (TEOS) or aminopropyltrimethoxysilane (APTS) (both available from Sigma, St. Louis). To coat cores, such reactive silicates are simply added to a solution of nanoparticle cores (e.g., the microemulsion in which the cores were prepared) along with a reducing agent such as ammonium hydroxide or NaOH. The mixture can be stirred for a suitable amount of time to allow the cores to become coated with silica.

Thickness of the silica coating, and the reaction rate for the formation of silica coating are dependent on the amount of reactive silicate added, reaction time, amount of reducing agent added, and reverse micelle size (where coating is performed in a water-in-oil microemulsion). Increasing the concentration of the reducing agent (e.g, [NH$_4$OH]) to reactive silicate concentration (e.g., [TEOS]) generally results in a thicker coating forming after a given reaction time. Increasing the concentration of polar liquid (e.g., water) to reactive silicate concentration generally results in a thinner coating forming after a given reaction time. The precise reaction conditions for controlling the thickness of the coating will vary according to the particular agent used, the core material, etc. These, however, can be determined empirically by simple experiments varying the concentrations of reagents and reaction times and conditions.

Methods within the invention can also include a step of functionalizing (i.e., derivatizing with one or more functional chemical groups) coated nanoparticles made as described above. Numerous known methods for attaching functional groups to silica can be adapted for use in the present invention. See, e.g., Ralph K. Iler, *The Chemistry of Silica: Solubility, Polymerization, Colloid and Surface Properties, and Biochemistry*, Wiley-Interscience, NY, 1979; VanDerVoort, P. and Vansant, E. F., Journal of Liquid Chromatography and Related Technologies, 19:2723–2752, 1996; and *Immobilized Enzymes. Antigens, Antibodies, and Peptides: Preparation and Characterization*, Howard H. Weetall (ed.), M. Dekker, NY, 1975. A typical process for adding functional groups to silica-coated nanoparticles involves treating the nanoparticles with a silanizing agent that reacts with and couples a chemical group to the silica surface of the nanoparticles. The chemical group can itself be the functional group, or it can serve as a substrate to which functional groups can be coupled.

For example, in an exemplary method, silica-coated nanoparticles are prepared as described above and the particle surfaces are silanized using trimethylsilylpropyl-diethylenetriamine (DETA), a silanization agent that attaches primary amine groups to silica surfaces. Antibodies or other proteins can then be covalently coupled to the silanized surface using the cyanogen bromide (CNBR) method. As one example, CNBR-mediated coupling can be achieved by suspending silica-coated nanoparticles previously silanized with DETA in a 2 M sodium carbonate buffer and ultrasonicating the mixture to create a particle suspension. A solution of CNBR (e.g., 2 g CNBR/1 ml acetonitirile) is then added to the particle suspension to activate the nanoparticles. After washing the nanoparticles with a neutral buffer (e.g., PBS, pH 8), an antibody solution is added to the activated nanoparticle suspension causing the antibodies to become bound to the nanoparticles. A glycine solution can also be added to the antibody-coated nanoparticles to block any remaining unreacted sites.

Methods of Using Nanoparticles

Figure 3B:
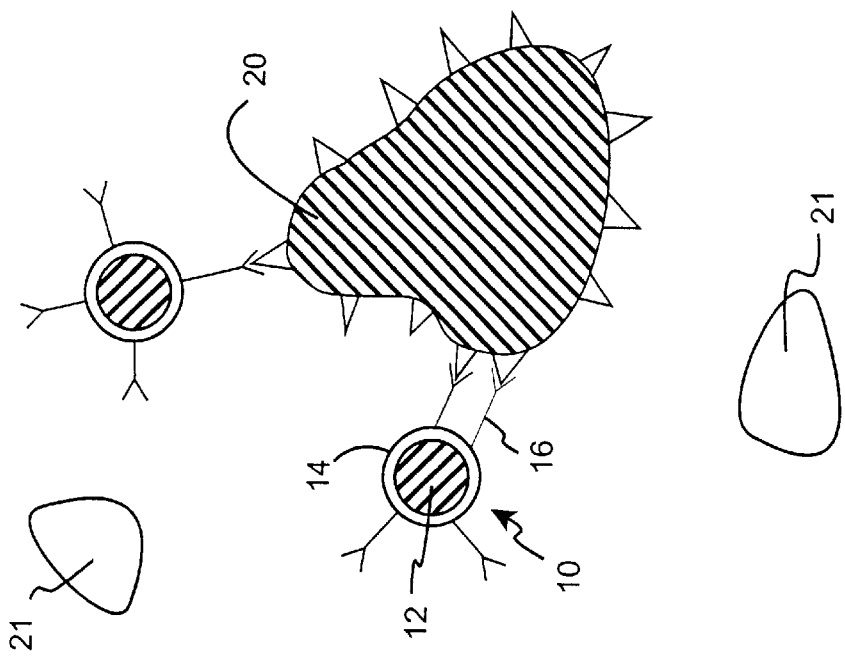
FIGS. 3A–D are schematic views illustrating a method of the invention.
Figure 3A:
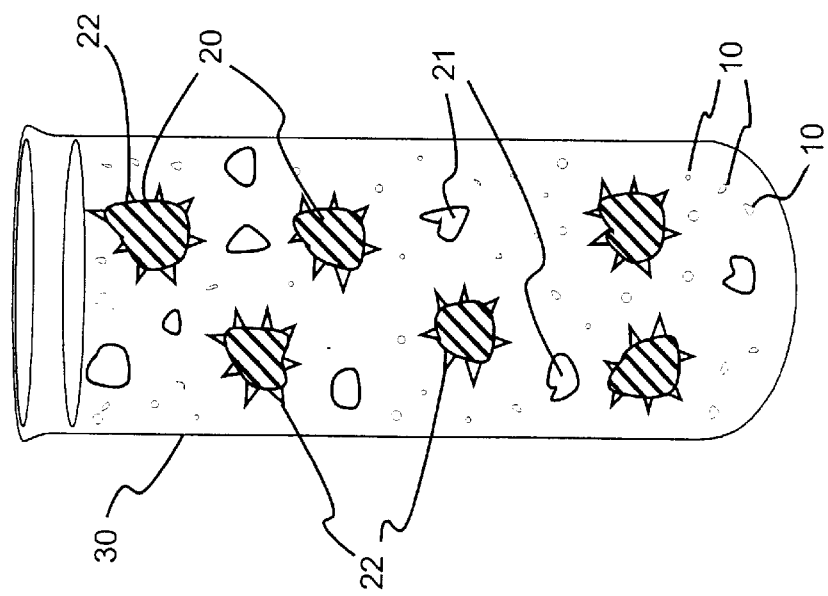
Figure 3D:
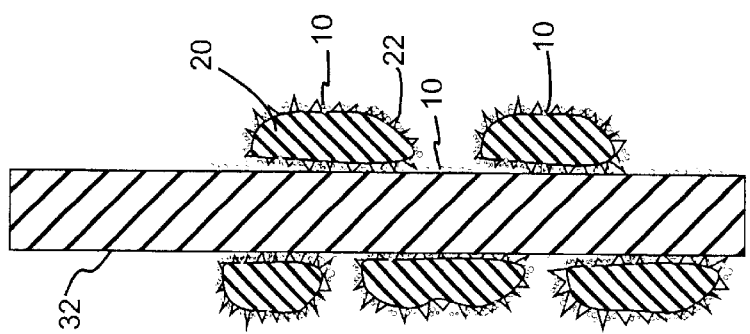
Figure 3D:
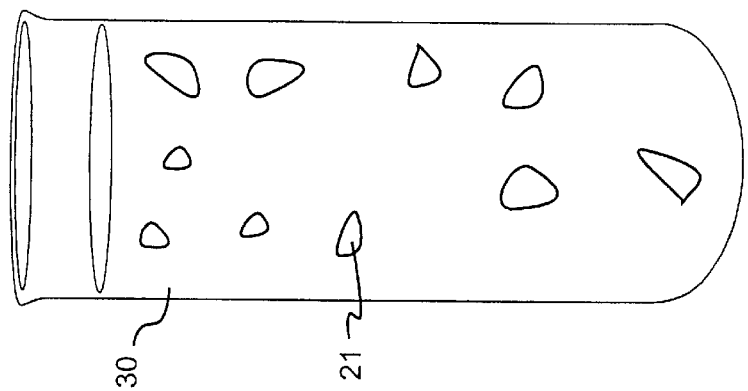
Figure 3C:
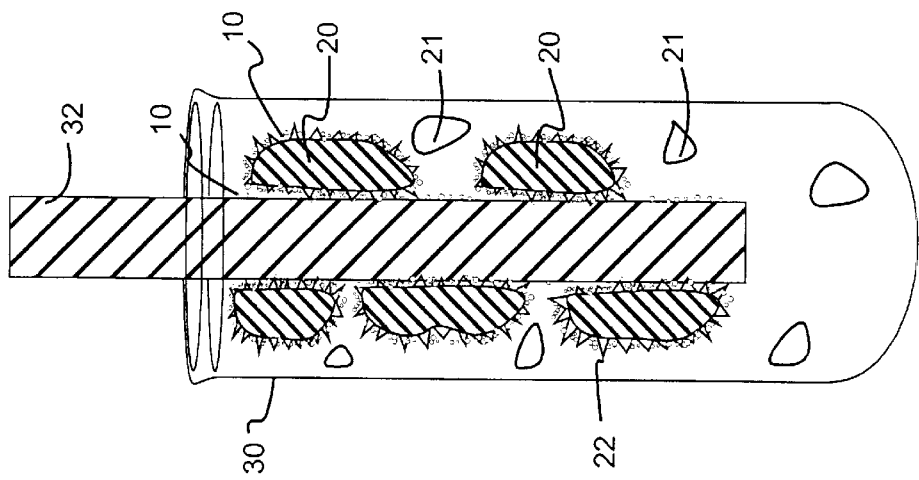

Nanoparticles of the invention to isolate cells (e.g., eukaryotic or prokaryotic cells). One such method is illustrated in FIG. 3. Referring to FIG. 3A, antibody-derivatized magnetic nanoparticles 10 are shown mixed with target cells 20 and non-target cells 21 in container 30. Target cells 20 express a target antigen 22 on their surface, while non-target cells 21 do not. In the nanoparticles shown, core 12 includes a ferrous material such as magnetite or maghemite, and functional groups 16 include an antibody that can specifically bind target antigen 22. Referring now to FIG. 3B, nanoparticle 10 is shown physically binding target cell 20 via the interaction of functional groups 16 and target antigen 22. Such binding spontaneously results when nanoparticle 10 and target cell 20 are mixed together in container 30 under conditions which allow antibody-antigen binding (e.g., about room temperature, neutral to slightly basic pH in a low salt buffer). Non-target cells 21 do not specifically bind nanoparticles 10 because they do not express target antigen 22. As shown in FIG. 3C, application of a magnetic field to the nanoparticle-cell mixture by insertion of magnet 32 into container 30 causes nanoparticles 10 and bound target cells 21 to associate with magnet 32. Referring to FIG. 3D, by removing magnet 32 from container 30, target cells 20 can be isolated. Cells 20 can be separated from nanoparticles 10 using an excess of soluble antigen.

Many other applications are specifically envisioned including, for example, cell labeling (see Example 8 below), targeted drug or gene delivery, biosensors, magnetic recording media, magnetic resonance imaging, and use in micro- or nano-sized machines. For example, cytotoxic drugs or viral vectors carrying therapeutic genes can be attached to the functional groups on the surface of nanoparticles. These nanoparticles can then be dispersed in a pharmaceutically acceptable carrier (e.g., USP grade saline) and administered to a patient (e.g., by intravenous injection). Magnetic fields can then be used to concentrate the virus or drug at the delivery site to enhance site-specific uptake (e.g., by placing a magnet at the site). Drugs coated onto nanoparticles can be further contained within a time-release coating (e.g., a biodegradable sugar) so that the drug can accumulate at the site before becoming active.

In other envisioned examples, fluorescence-based biosensors can be attached to the particles. The resulting particles can be manipulated by magnetic means into specific target sites (specific locations in isolated cells), and used to monitor biochemical processes in situ. The nanoparticles of the invention are also thought to be useful for enhancing Magnetic Resonance Images (MRI). For example, as described above, antibody or ligand-coated nanospheres can be caused to accumulate at sites in the body where the target antigen or receptor is concentrated or located. In comparison to non-targeted MRI contrast agents, the increased concentration of particles at a targeted site will enhance the contrast in an MRI.

Nanoparticles manufactured in a stable, single domain size range that allows a remnant magnetization to be preserved are envisioned to be useful in binary magnetic recording applications where they can be substituted for the simple iron particles used in conventional magnetic storage devices. For example, arrays of ferrite-doped silica particles could be tailored for minimum magnetostatic interactions to permit individual nanoparticles to be magnetized either parallel or antiparallel to their easy axis of magnetization for binary data storage applications. And because stable single domain particles are able to transduce applied magnetic fields as mechanic motion (i.e. a torque can be exerted on the particle when a magnetic field is applied at an angle to the easy axis of magnetization), arrays of these nanoparticles of the invention could find use as mechanical micro- or nano-machines. One particular example would be micromechanical gate activation upon application of an external magnetic field.

EXAMPLES

Example 1

Preparation of Silica-Coated Magnetite Nanoparticles by Microemulsion (A) A 0.27 M bis (2-ethylhexyl) sulfosuccinate sodium salt (Aerosol OT or AOT ) solution was prepared by dissolving 12 g AOT in 10 ml isooctane. An aliquot of ultra-pure water was purged for one hour with $N_2$ gas. A stock solution of 1 M Fe(II) was prepared by dissolving 0.278 g $FeSO_4 7H_2O$ in 1 ml of the nitrogen purged water. Similarly, a stock solution of 1.5 M Fe(III) was prepared by dissolving 0.4055 g $FeCl_3.6\ H_2O$ (0.4055 gm) in 1 ml of the nitrogen purged water. In a glass container, 25 $\mu$l of the 1 M Fe(II) solution and 25 $\mu$l of the 1.5 M Fe(III) solution were added to a 5 ml aliquot of the AOT solution under a nitrogen atmosphere, and the resulting Fe/AOT mixture was magnetically stirred for 1 hr to form a Fe/AOT solution. In another container, 100 $\mu$l $NH_4OH$ (28–30 wt %) was added to another 5 ml aliquot of the AOT solution, and the resulting $NH_4OH$/AOT mixture was magnetically stirred for 1 hr to form a $NH_4OH$/AOT solution . In absence of magnetic field, the $NH_4OH$/AOT solution was added dropwise to the Fe/AOT solution with vigorous mechanical stirring for 1 hr.

Initially a light yellow solution formed. This solution turned brown (without any precipitate formation) as magnetite nanoparticles formed. 50 μl of tetraethylorthosilicate (TEOS) was then added to the resulting brown solution and mechanical stirring was continued for an additional 24 hrs. Silica-coated uniform-sized nanoparticles in powder form were obtained by coagulating the colloidal microemulsion with acetone, and then filtering and washing the particles with acetone and ethanol several times with each solvent. In some cases, 50% (v/v) solution of ethanol/water was also used for washing.

(B) 1.78 g of AOT was dissolved in 20.0 ml of isooctane. The resulting solution was mixed using a sonicator and flushed with nitrogen. 100 μL each of $N_2$-flushed 0.10 M $FeSO_4$ and 0.15 M $FeCl_3$ (both prepared in water) were then added and mixed into the solution to form a microemulsion. 100 μL of $N_2$-flushed solution of 2.0 M NaOH was then added, and the resulting microemulsion was sonicated for 1 hour while being continuously flushed with $N_2$. 10 μL of TEOS was then added to the sonicated microemulsion, and the mixture was allowed to react overnight. The isooctane contained in the microemulsion was then evaporated and the remaining gel was dissolved in ethanol. This solution was centrifuged to pellet the nanoparticles and the supernatant was discarded. After washing 3 or 4 more times with ethanol, the resulting nanoparticles were subjected to TEM which showed that nanoparticles having a diameter of approximately 3–5 nm were produced. A silica shell was observed as a translucent halo about 2–3 nm thick surrounding the denser core.

(C) A microemulsion I (ME I) was prepared by first dissolving 8.89 g AOT in 40.0 ml isooctane to form a first solution. 1.2 ml $H_2O$ and 6.0 ml $FeSO_4$ was then added and the mixture was sonicated to form ME I. In another glassware, a microemulsion II (ME II) was similarly prepared by first dissolving 8.89 g AOT and dissolve in 40.0 ml isooctane to form a second solution. 3.2 ml $H_2O$ and 4.0 ml $NH_4OH$ was added to the second solution, which was then mixed for about 30 minutes to form ME II. 10 μL TEOS was added to ME II, and the mixture was allowed to react for about 2 hours. Using a glass syringe, ME II was slowly added to ME I, and the reaction mixture thus formed was sonicated for 24 hours. As described in (B) above, the isooctane was then evaporated, the remaining gel was dissolved in ethanol and centrifuged to recover the formed nanoparticles which were washed 3 or 4 times with additional ethanol. TEM showed that nanoparticles having a diameter of approximately 25 nm were produced. A silica shell was observed as a translucent halo about 5 nm thick surrounding the denser core.

Example 2

Preparation of Dye-doped Silica-Coated Nanoparticles (A) Preparation of Eu/Bpy ($Eu^{3+}$/2,2'-dipyridyl)-doped silica nanoparticles in cetyltrimethylammonium bromide (CTAB)/n-hexane/n-hexanol (cosurfactant)/water water-in-oil microemulsions. 90 ml of a water-in-oil microemulsion stock solution was prepared by mixing together 2.916 g CTAB, 75 ml n-hexane, 15 ml n-hexanol and 880 μl water using a magnetic stirrer. 10 ml of the stock solution was equally divided into two 5 ml aliquots. 50 μl TEOS and 5 μl 0.1 M Eu/Bpy (aqueous solution) was added to one of the 5 ml aliquots and the mixture was stirred for 1 hr to form a TEOS/Eu/Bpy solution. 137 μl $NH_4OH$ was added to the other 5 ml aliquot and the mixture was stirred for 1 hr to form an $NH_4OH$ solution. The $NH_4OH$ solution was then added dropwise to the TEOS/Eu/Bpy solution and the resulting mixed solution was stirred overnight. The water to surfactant molar ratio of the mixed solution was 15 (water:surfactant). Eu/Bpy-doped silica nanoparticles were isolated in powder form by adding 25 ml of acetone to the microemulsion of the mixed solution, centrifuging the resultant mixture for 15 minutes at 10,00 RPM in a microcentrifuge to pellet the nanoparticles, the supernatant was removed and the remaining nanoparticles were washed several times with acetone or an ethanol/water solution to further remove surfactant and other microemulsion components. The washed nanoparticles were then dried over acetone.

(B) Ru/Bpy [$Ru^{II}(Bpy)_3$]-doped silica nanoparticles in triton X-100 (TX-100)/cyclohexane/n-hexanol (cosurfactant)/water water-in-oil microemulsions. 10 ml of a water-in-oil microemulsion was prepared by mixing 7.5 ml cyclohexane, 1.8 ml n-hexanol, 1.77 ml TX-100, 340 μl water and 140 μl 0.1 M $Ru^{II}(Bpy)_3$ (aqueous solution) for 1 hr with a magnetic stirrer. The resulting solution was then divided into two 5 ml aliquots. 100 μl TEOS was added to one aliquot and the mixture was stirred for 30 minutes to form a TEOS solution. 60 μl of $NH_4OH$ was added to the other 5 ml aliquot and the mixture was stirred for 30 minutes to form a $NH_4OH$ solution. The $NH_4OH$ solution was then added to the TEOS solution dropwise for a period of 10 minutes and the resulting mixed solution was stirred overnight. Ru/Bpy doped silica nanoparticles were isolated as described above in (A).

Example 3

Preparation of Metal-Doped Silica-Coated Nanoparticles 10 ml of a TX-100/cyclohexane/n-hexanol(cosurfactant)/waterwater-in-oil microemulsion stock solution was prepared as described in Example 2(A). The stock solution was equally divided into two 5 ml aliquots. 30 μl of a 1M aqueous solution of silver nitrate ($AgNO_3$) was added to one of the 5 ml aliquots and the mixture was stirred for about 30 minutes to form a $AgNO_3$ solution. 11 μl of a 2M aqueous solution of sodium borohydride ($NaBH_4$) was added to the other 5 ml aliquot and the mixture was stirred for about 30 minutes to form an $NaBH_4$ solution. The $NaBH_4$ solution was then added dropwise to the $AgNO_3$ solution for the period of 15 minutes to form a reaction mixture. After 5 minutes, 10 μl of TEOS was added and the resulting mixture stirred for another 15 minutes. 10 μl of a $NH_4OH$ solution was then added and stirring was continued overnight. The Ag-doped silica nanoparticles were isolated similar to the procedure described in Example 2(A), i.e., by adding 25 ml of acetone to the microemulsion, filtering, washing several times with an ethanol/water solution to remove surfactant, and finally drying over acetone.

Using a variation of this method cadmium sulfide (CdS)-doped silica nanoparticles were also prepared. In this case, cadmium nitrate and ammonium sulfide were used in place of silver nitrate and sodium borohydride, respectively.

Example 4

Preparation of Pigments

A new class of pigments was prepared using regular inorganic salts including potassium permanganate, potassium dichromate, nickel sulfate, cobalt-chloride, iron(III)

chloride, and copper nitrate. While these salts are highly water soluble, they become completely insoluble when coated with silica, and thus behaved as pigments. All were colored and photostable.

These pigments was prepared as described for the Ru/Bpy doped silica nanoparticles described above in Example 2(B), except that a 0.1M salt solution (e.g., potassium permanganate, potassium dichromate, nickel sulfate, cobalt-chloride, iron(III) chloride, and copper nitrate) was used in place of the 0.1 M $Ru^{II}(Bpy)_3$ solution, and an additional 100 µl TEOS and 60 µl $NH_4OH$ were added to the mixed solution 12 hrs after the 10 ul addition of $NH_4OH$. Pigment particles were separated from the mixture after 24 hrs.

Example 5

Characterization of Nanoparticles

Transmission electron microscopy (TEM) and other analyses were used to characterize of the size of various nanoparticles made according to the invention. As one example, $Ru^{II}(Bpy)_3$ nanoparticles were prepared as described in Example 2(B) and subjected to TEM. By analyzing photographs of the TEM images, it was determined that the $Ru^{II}(Bpy)_3$ nanoparticles had a core size of about 20 nm (standard deviation=+/−2 nm) and an overall particle size of about 100 nm (standard deviation=+/−10 nm). Smaller and larger silica-coated nanoparticles were also prepared by varying the preparation conditions specified above. For example, those with core sizes even as small as 2 nm (e.g., sized to prepare quantum dots) with constant or varied thickness (as large as 300 nm) of the outer silica coating have been prepared. Nanoparticles useful as pigments (see Example 5) were also subjected to TEM which showed that such particles were sized between 0.2 and 0.3 µm. In other analyses, compared to commercially available conventional dyes, dye-doped nanoparticles made according to the invention proved extremely resistant to bleaching even after strong excitation from a laser source. Similarly, no fluorescence quenching was observed in fluorescent dye-doped nanoparticles.

Example 6

Preparation of a Nanoparticle-based Chemosensor

Dye-doped, silica-coated nanoparticles were prepared using a water-in-oil microemulsion technique. The water-in-oil microemulsion was prepared first by mixing Triton X-100 (TX-100), cyclohexane, n-hexanol (4.2:1:1 VN) and an adequate amount of water. An aqueous dye solution $(Ru^{II}(Bpy)_3)$; (see example 3B above) was then added to the microemulsion in such a way that the water to surfactant molar ratio was kept constant at 10. The final dye concentration in the mixture was 0.1 M. TEOS was then added to the mixture. A polymerization reaction was initiated by adding $NH_4OH$ (volume ratio of TEOS to $NH_4OH$ was 1.7), and the reaction was allowed to continue for 12 hours. After the reaction was complete, the dye-doped silica nanoparticles were isolated by adding acetone to the reaction, followed by centrifuging and washing with ethanol and water for several times. The nanoparticles were then stored in aqueous solution for later usage.

The dye-doped silica nanoparticles produced were uniform in size, as characterized by transmission electron microscopy (TEM) and atomic force microscopy (AFM). A TEM image of the dye-doped silica particles showed that the particles were 60±10 nm in size and uniform. At a higher resolution, the luminescent complex of RuBpy dye aggregates were also visible as darker dots embedded inside the silica sphere due to the presence of heavy metal atom in these dye molecules. These individual dye aggregates were as small as 1 nm.

To investigate whether the RuBpy molecules doped inside the silica network could function as an oxygen sensor, the fluorescence emission spectra of free RuBpy molecules was compared to that of the RuBpy-doped nanoparticles at various air pressures. With the free RuBpy dye molecules, the intensity of the emission was greatly decreased as the air pressure was increased from 1 to 14 psi. In contrast, under the same conditions, no significant change in the emission spectra for the dye-doped silica-coated nanoparticles was observed, indicating that the silica network was essentially impermeable to oxygen molecules. In other experiments, the dye-doped silica-coated nanoparticles also showed excellent photostability even upon intensive laser illumination.

Example 7

Functionalized Silica-Coated Nanoparticles

The dye-doped, silica-coated nanoparticles of Example 6 were derivatized with antibodies by first silanizing the particle surfaces with DETA, a silanization agent that attaches the primary amine group to silica surfaces. Using fluorescamine, a non-fluorescent molecule that becomes highly fluorescent upon reacting with the primary aliphatic amine group (Cordek, J. Wang, X and Tan W., *Anal Chem*, 71, 1529–1533, 1999; Chung, L. A. *Anal Biochem.* 1997, 248,195), the presence of amine group on the surface of the nanoparticles was confirmed.

After surface silanization with DETA, an antibody (mouse anti-human CD10) was immobilized onto the silanized silica surface using the cyanogen bromide (CNBR) method. Dye-doped particles (26 g) were prepared as described in Example 6, dried, and then suspended in 9.0 ml 2 M sodium carbonate solution (activation buffer) using ultrasonication. A solution of CNBR in acetonitrile (1.0 gm of CNBR dissolved in 0.5 ml acetonitrile) was then added dropwise to the particle suspension (10 mg/ml) under stirring for 5 minutes at room temperature. The resulting CNBR-activated particles were washed twice with ice-cold water and twice with PBS buffer (pH 8.0).

40 µl of the antibody diluted in PBS buffer (pH 8.0) was then added to the surface modified particles, and stirring was continued for 24 hours at 4° C. The resulting antibody-derivatized nanoparticles were then treated with 10 ml of 0.03 M glycine solution for 30 minutes to block any remaining reactive sites. The final product was washed, re-suspended in PBS (pH 8.0) buffer and stored at 4° C. for future usage. No change in the optical and spectroscopic properties of the nanoparticles was observed.

Example 8

Cell Labeling

Mononuclear lymphoid cells (about 2 million cells/ml) were obtained as a suspension in the cell culture medium. The cell suspension was incubated for 2 hours with the anti-CD10 immobilized nanoparticles described in Example 7. After incubation, the cell suspension was imaged with both optical microscopy and fluorescence microscopy. The microscopic analysis revealed that most of the cells were labeled (indicated by the bright emission of the dye-doped particles). The optical images correlated well with the fluorescence images. In control experiments using non-antibody derivatized dye-doped nanoparticles, no labeling of cells was observed. In the labeled cells, the signal-to-noise ratio (i.e., the ratio between the intensities of the bright and the dark areas in the fluorescence image) was over 500.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. A plurality of nanoparticles having a mean size of less than 1 micron, each of said nanoparticles comprising (a) a core comprising a pigment and (b) a silica shell enveloping the core, wherein the pigment is an inorganic salt selected from potassium permanganate, potassium dichromate, nickel sulfate, cobalt-chloride, iron(III) chloride, and copper nitrate.

2. The plurality of nanoparticles of claim 1, wherein the mean size is between 1 nm and 300 nm.

3. The plurality of nanoparticles of claim 1, wherein the mean size is between 2 nm and 10 nm.

4. The plurality of nanoparticles of claim 1, wherein the silica shell is derivatized with a functional group.

5. The plurality of nanoparticles of claim 4, wherein the functional group is a protein.

6. The plurality of nanoparticles of claim 5, wherein the functional group is an antibody.

7. The plurality of nanoparticles of claim 4, wherein the functional group is a nucleic acid.

8. The plurality of nanoparticles of claim 4, wherein the functional group is a substance selected from the group consisting of biotin and streptavidin.

9. A plurality of nanoparticles having a mean size of less than 1 micron, each of said nanoparticles comprising (a) a core comprising a dye, and (b) a silica shell enveloping the core.

10. The plurality of nanoparticles of claim 9, wherein the dye is selected from the group consisting of Ruthenium-tris (2,2'-bipyridyl)dichloride and Europium-bis(2,2'bipyridyl) trichloride.

11. The plurality of nanoparticles of claim 9, wherein the mean size is between 1 nm and 300 nm.

12. The plurality of nanoparticles of claim 9, wherein the mean size is between 2 nm and 10 nm.

13. The plurality of nanoparticles of claim 9, wherein the silica shell is derivatized with a functional group.

14. A The plurality of nanoparticles of claim 13, wherein the functional group is a protein.

15. The plurality of nanoparticles of claim 13, wherein the functional group is an antibody.

16. The plurality of nanoparticles of claim 13, wherein the functional group is a nucleic acid.

17. The plurality of nanoparticles of claim 13, wherein the functional group is a substance selected from the group consisting of biotin and streptavidin.

18. A plurality of nanoparticles having a mean size of between 2 nm and 10 nm, each of said nanoparticles comprising (a) a core comprising a metal and (b) a silica shell enveloping the core.

19. The plurality of nanoparticles of claim 18, wherein the core is magnetic.

20. The plurality of nanoparticles of claim 19, wherein the core is superparamagnetic.

21. The plurality of nanoparticles of claim 19, wherein the core has a fixed magnetic moment.

22. The plurality of nanoparticles of claim 18, wherein the core has a spherical shape.

23. The plurality of nanoparticles of claim 18, wherein the core has an oblong shape.

24. The plurality of nanoparticles of claim 18, wherein the core has a tube-like shape.

25. The plurality of nanoparticles of claim 18, wherein the metal is magnetite.

26. The plurality of nanoparticles of claim 18, wherein the metal is maghemite.

27. The plurality of nanoparticles of claim 18, wherein the metal greigite.

28. The plurality of nanoparticles of claim 18, wherein the silica shell is derivatized with a functional group.

29. The plurality of nanoparticles of claim 28, wherein the functional group is a protein.

30. The plurality of nanoparticles of claim 28, wherein the functional group is an antibody.

31. The plurality of nanoparticles of claim 28, wherein the functional group is a nucleic acid.

32. The plurality of nanoparticles of claim 28, wherein the functional group is a substance selected from the group consisting of biotin and streptavidin.

33. A plurality of nanoparticles having a mean size of less than 1 micron, each of said nanoparticles comprising (a) a core comprising a metal and (b) a silica shell enveloping the core, wherein the size distribution of the nanoparticles has a standard deviation of no more than 25 percent.

34. The plurality of nanoparticles of claim 33, wherein the core is magnetic.

35. The plurality of nanoparticles of claim 34, wherein the core is superparamagnetic.

36. The plurality of nanoparticles of claim 34, wherein the core has a fixed magnetic moment.

37. The plurality of nanoparticles of claim 33, wherein the core has a spherical shape.

38. The plurality of nanoparticles of claim 33, wherein the core has an oblong shape.

39. The plurality of nanoparticles of claim 33, wherein the core has a tube-like shape.

40. The plurality of nanoparticles of claim 34, wherein the metal is magnetite.

41. The plurality of nanoparticles of claim 34, wherein the metal is maghemite.

42. The plurality of nanoparticles of claim 34, wherein the metal greigite.

43. The plurality of nanoparticles of claim 33, wherein the silica shell is derivatized with a functional group.

44. The plurality of nanoparticles of claim 43, wherein the functional group is a protein.

45. The plurality of nanoparticles of claim 43, wherein the functional group is an antibody.

46. The plurality of nanoparticles of claim 43, wherein the functional group is a nucleic acid.

47. The plurality of nanoparticles of claim 43, wherein the functional group is a substance selected from the group consisting of biotin and streptavidin.

48. The plurality of nanoparticles of claim 33, wherein the core consists of metal and each of the nanoparticles comprises a structure consisting of the core enveloped by the silica shell.

49. The plurality of nanoparticles of claim 33, wherein the mean size is 10 nm.

50. The plurality of nanoparticles of claim 33, wherein the mean size is 15 nm.

51. The plurality of nanoparticles of claim 33, wherein the mean size is 20 nm.

52. The plurality of nanoparticles of claim 33, wherein the mean size is 25 nm.

53. The plurality of nanoparticles of claim 33, wherein the mean size is 30 nm.

54. The plurality of nanoparticles of claim 33, wherein the mean size is 35 nm.

55. The plurality of nanoparticles of claim 33, wherein the mean size is 50 nm.

56. A plurality of nanoparticles having a mean size of less than 1 micron, each of said nanoparticles comprising (a) a core comprising Ag, and (b) a silica shell enveloping the core.

57. The plurality of nanoparticles of claim 56, wherein the mean size is between 1 nm and 300 nm.

58. The plurality of nanoparticles of claim 56, wherein the mean size is between 2 nm and 10 nm.

59. The plurality of nanoparticles of claim 56, wherein the silica shell is derivatized with a functional group.

60. The plurality of nanoparticles of claim 59, wherein the functional group is a protein.

61. The plurality of nanoparticles of claim 59, wherein the functional group is an antibody.

62. The plurality of nanoparticles of claim 59, wherein the functional group is a nucleic acid.

63. The plurality of nanoparticles of claim 59, wherein the functional group is a substance selected from the group consisting of biotin and streptavidin.

* * * * *

UNITED STATES PATENT AND TRADEMARK OFFICE
CERTIFICATE OF CORRECTION

PATENT NO. : 6,548,264 B1 Page 1 of 1
APPLICATION NO. : 09/572469
DATED : April 15, 2003
INVENTOR(S) : Tan et al.

It is certified that error appears in the above-identified patent and that said Letters Patent is hereby corrected as shown below:

Column 17, line 51, replace "A The Plurality" with --The Plurality--.

Column 18, line 14, replace "metal greigite" with --metal is greigite--.

Column 18, line 48, replace "metal greigite" with --metal is greigite--.

Signed and Sealed this

Fifth Day of June, 2007

JON W. DUDAS
*Director of the United States Patent and Trademark Office*